United States Patent [19]

Zoller et al.

[11] Patent Number: 5,424,293
[45] Date of Patent: *Jun. 13, 1995

[54] PHENYLIMIDAZOLIDINE DERIVATIVES AND THEIR USE

[75] Inventors: Gerhard Zoller, Schöneck; Bernd Jablonka, Bad Soden; Melitta Just, Langen; Otmar Klingler, Rodgau; Gerhard Breipohl, Frankfurt am Main; Jochen Knolle, Kriftel; Wolfgang König, Stallwang, all of Germany

[73] Assignee: Cassella AG, Frankfurt am Main, Germany

[*] Notice: The portion of the term of this patent subsequent to Jun. 6, 2012 has been disclaimed.

[21] Appl. No.: 95,905

[22] Filed: Jul. 22, 1993

[30] Foreign Application Priority Data

Jul. 24, 1992 [DE] Germany .................. 42 24 414.5

[51] Int. Cl.$^6$ .................. A61K 37/02; C07D 233/76; C07D 233/96
[52] U.S. Cl. .................. 514/20; 548/319.5; 514/19; 514/18
[58] Field of Search .................. 548/319.5; 514/20, 18, 514/19

[56] References Cited

FOREIGN PATENT DOCUMENTS 566919 10/1993 European Pat. Off. .......... 548/319.5

OTHER PUBLICATIONS

Bennett et al., J. Clin. Invest. 64, Nov. 1979, 1393–1401.
Kornecki et al., J. Biol. Chem., 256(11), 5695–5701 (1981).
Marguerie et al., J. Biol. Chem., 254(12), 5357–5363 (1979).
Marguerie et al., J. Biol. Chem., 255(1), 154–161 (1980).

Primary Examiner—Robert W. Ramsuer
Assistant Examiner—Fiona T. Powers
Attorney, Agent, or Firm—Perman & Green

[57] ABSTRACT

Phenylimidazolidine derivatives of the general formula I

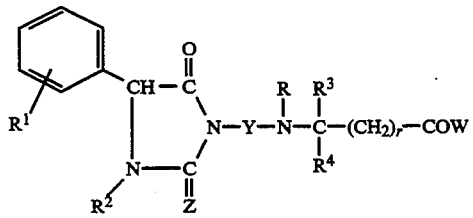

in which, for example,
Y denotes —$CH_2$—$CH_2$—CO—
r denotes 0 to 3
Z denotes oxygen
W denotes hydroxyl
$R^1$ denotes —NH—C(=NH)—$NH_2$
R, $R^2$, $R^3$ denote hydrogen
$R^4$ denotes —CO—$NHR^5$, where —NH—$R^5$ represents an α-amino acid radical, have useful pharmacological properties such as inhibition of platelet aggregation and osteoclast binding to the bone surfaces.

6 Claims, No Drawings

PHENYLIMIDAZOLIDINE DERIVATIVES AND THEIR USE

The present invention relates to phenylimidazolidine derivatives, their preparation and their use as inhibitors of blood platelet aggregation.

Hydantoin derivatives having platelet aggregation-inhibiting action are described in EP-A 449,079, and in the unpublished German Patent Application P 41 26 277 8. Further research has shown that the compounds of the present invention are also potent inhibitors of blood platelet aggregation.

The present invention relates to compounds of the general formula I

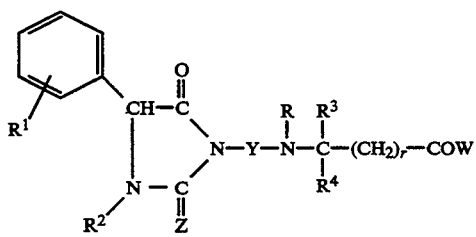
(I)

in which

Y denotes —$(CH_2)_m$—CO—, where m represents an integer from 1 to 4, or

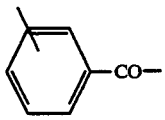

r denotes a number from 0 to 3;

Z denotes oxygen or sulphur;

W denotes hydroxyl, $(C_1-C_{28})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$(C_1-C_{18})$-alkylamino;

$R^1$ denotes —$(CH_2)_n$—NH—X or —$(CH_2)_p$—C(=NH)—NH—$X^1$, where n and p represent a number 0 to 3, X, $X^1$ denote hydrogen, $(C_1-C_6)$-alkyl, $(C_1-C_6)$-alkoxycarbonyl, $(C_1-C_6)$-alkylcarbonyl, $(C_1-C_{18})$-alkylcarbonyl-oxy-$(C_1-C_6)$-alkoxycarbonyl, $(C_6-C_{14})$-aryloxycarbonyl, which can also be substituted in the aryl radical, $(C_6-C_{14})$-aryl-$(C_1-C_6)$-alkoxycarbonyl which can also be substituted in the aryl radical, cyano, hydroxyl, $(C_1-C_6)$-alkoxy or amino, and X additionally denotes a radical of the formula II

R'—NH—C(=N—R'') (II)

where

R', R'' independently of one another denote hydrogen, $(C_1-C_6)$-alkyl, $(C_1-C_6)$-alkoxycarbonyl, $(C_1-C_6)$-alkylcarbonyl, $(C_1-C_{18})$-alkylcarbonyl-oxy-$(C_1-C_6)$-alkoxycarbonyl, $(C_6-C_{14})$-aryloxycarbonyl, which can also be substituted in the aryl radical, $(C_6-C_{14})$-aryl-$(C_1-C_6)$-alkoxycarbonyl which can also be substituted in the aryl radical, cyano, hydroxyl, $(C_1-C_6)$-alkoxy or amino;

R, $R^2$ denote hydrogen or $(C_1-C_6)$-alkyl;

$R^3$ denotes hydrogen, phenyl or substituted phenyl;

$R^4$ denotes hydrogen, —$COOR^5$, CO—$N(CH_3)R^5$ or —CO—NH—$R^5$;

$R^5$ denotes hydrogen or $(C_1-C_{28})$-alkyl which is optionally mono- or polysubstituted by identical or different radicals from the series consisting of hydroxyl, hydroxycarbonyl, aminocarbonyl, mono or di-$(C_1-C_{18})$-alkylaminocarbonyl, amino-$(C_2-C_{14})$-alkylaminocarbonyl, amino$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-, alkylcarbonylamino-$(C_2-C_{14})$-alkylaminocarbonyl, phenyl-$(C_1-C_8)$-alkoxycarbonyl, which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, halogen, nitro, trifluoromethyl or a radical $R^6$, where $R^6$ denotes optionally substituted $(C_6-C_{14})$-aryl, optionally substituted $(C_6-C_{14})$-aryl-$(C_1-C_8)$-alkyl or a monocyclic or bicyclic 5- to 12-membered heterocyclic ring which can be aromatic, partially hydrogenated or completely hydrogenated and which, as the heteroelement, can contain one, two or three identical or different nitrogen, oxygen or sulphur atoms, or denotes a radical $R^7$, where the aryl radical and, independently thereof, the heterocyclic radical can be optionally monosubstituted or polysubstituted by identical or different radicals from the series consisting of $(C_1-C_{18})$-alkyl, $(C_1-C_{18})$-alkoxy, halogen, nitro, amino and trifluoromethyl;

$R^7$ denotes —$NR^8R^9$, —$OR^8$, —$SR^8$, an amino acid side chain, a natural or unnatural amino acid residue, imino acid residue, optionally N—$(C_1-C_8)$-alkylated or $(C_6-C_{14})$-aryl-$(C_1-C_8)$-alkylated azaamino acid residue or dipeptide residue, which can also be substituted in the aryl radical and/or in which the peptide bond can be reduced to NH—$CH_2$, and also their esters and amides, where free functional groups can optionally be substituted by hydrogen or hydroxymethyl or protected by protective groups customary in peptide chemistry, or denotes a radical —$COR^{7'}$, in which $R^{7'}$ is defined as $R^7$;

$R^8$ denotes hydrogen, $(C_2-C_{18})$-alkyl, optionally substituted $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkoxycarbonyl, where the alkyl groups can optionally be substituted by an amino group and/or where the aryl radicals can be monosubstituted or polysubstituted, preferably monosubstituted by identical or different radicals from the series consisting of $(C_1-C_8)$-alkyl, $(C_1-C_8)$-alkoxy, halogen, nitro, amino or trifluoromethyl, a natural or unnatural amino acid residue, imino acid residue, optionally N—$(C_1-C_8)$-alkylated or $(C_6-C_{14})$-aryl-$(C_1-C_8)$-alkylated azaamino acid residue or a dipeptide residue, which can also be substituted in the aryl radical and/or in which the peptide bond can be reduced to NH—$CH_2$; and $R^9$ denotes hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

and their physiologically tolerable salts.

Alkyl radicals can be straight-chain or branched. Preferred alkyl radicals are methyl, ethyl, n-propyl, i-propyl, n-butyl, i-butyl, sec-butyl and tert-butyl. The same applies to radicals such as alkoxy, alkoxycarbonyl or aralkyl. ($C_3$–$C_8$)-Cycloalkyl radicals are in particular cyclopropyl, cyclobutyl, cyclopentyl, cyclohexyl, cycloheptyl and cyclooctyl, which, however, can also be substituted by, for example, ($C_1$–$C_4$)-alkyl. Examples of substituted cycloalkyl radicals are 4-methylcyclohexyl and 2,3-dimethylcyclopentyl.

($C_6$–$C_{14}$)-Aryl groups are, for example, phenyl, naphthyl, biphenylyl or fluorenyl, phenyl and naphthyl being preferred. The same applies to radicals such as aralkyl or arylcarbonyl. Aralkyl radicals are in particular benzyl and also 1- and 2-naphthylmethyl, which can also be substituted. The aryl radicals, in particular phenyl radicals, can also be monosubstituted or polysubstituted, even if they occur as substituents of other radicals, by identical or different radicals from the series consisting of ($C_1$–$C_8$)-alkyl, ($C_1$–$C_8$)-alkoxy, halogen, nitro, amino or trifluoromethyl. Substituted aralkyl radicals are, for example, halobenzyl or ($C_1$–$C_4$)-alkoxybenzyl.

If phenyl is disubstituted, the substituents can be present in the 1,2-, 1,3- or 1,4-position to one another. In the case of disubstitution, the 1,3- and the 1,4-positions are preferred.

Heterocycles within the meaning of the above definitions are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxalinyl, quinazolinyl, cinnolinyl or a benzofused, cyclopenta-, cyclohexa- or cyclohepta-fused derivative of these radicals.

These heterocycles can be substituted on a nitrogen atom by oxides, ($C_1$–$C_7$)-alkyl, for example methyl or ethyl, phenyl or phenyl-($C_1$–$C_4$)-alkyl, for example benzyl, and/or on one or more carbon atoms by ($C_1$–$C_4$)-alkyl, halogen, hydroxyl, ($C_1$–$C_4$)-alkoxy, for example methoxy, phenyl-($C_1$–$C_4$)-alkoxy, for example benzyloxy, or oxo and can be partially or completely saturated.

Radicals of this type are, for example, 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, -2-, -3- or -4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro-or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, for example 2-, 3- or 4-N-methylpyrrolidinyl, piperazinyl, morpholinyl, thiomorpholinyl, tetrahydrothienyl, benzodioxolanyl.

Halogen represents fluorine, chlorine, bromine or iodine, in particular fluorine or chlorine.

Natural and unnatural amino acids can be present, if they are chiral, in the D- or L-form. α-Amino acids are preferred. For example, the following may be mentioned (cf. Houben-Weyl, Methoden der organischen Chemie (Methods of organic chemistry), Volume XV/1 and 2, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2(p-tolyl)-2-phenylaminoacetic acid and 2-(p-chlorophenyl)aminoacetic acid.

Amino acid side chains are understood as meaning side chains of natural or unnatural amino acids. Azaamino acids are natural or unnatural amino acids, the central component —CHR— or —CH$_2$— being replaced by —NR— or —NH— respectively.

Suitable radicals of an imino acid are in particular radicals of heterocycles from the following group:

Pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decanhydroquinoline-2-carboxylic acid; octahydrocyclopenta[b]pyrrole-2-carboxylic acid; 2-aza-bicyclo-[2.2.2]octane-3-carboxylic acid; 2-azabicyclo[2.2.1.]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]-heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]-decane-3carboxlic acid; decahydrocyclohepta[b]pyrrole-2-carboxylic acids; decahydrocycloocta[c]pyrrole-2-carboxlic acid; octahydrocyclopenta[c]pyrrole-2-carboxylic acid; octahydroisoindole-1-carboxylic acid; 2,3,3a,4,6a-hexahydrocyclopenta[b-]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid; which can all be optionally substituted (see the following formulae):

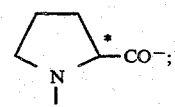

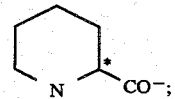

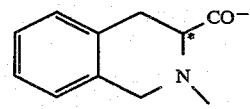

-continued
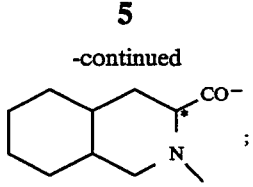
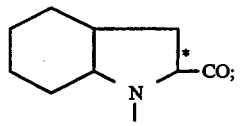
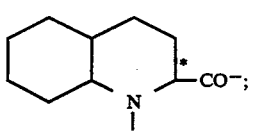
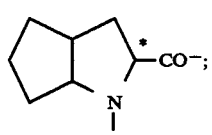
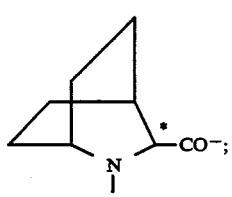
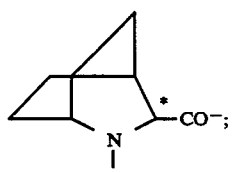
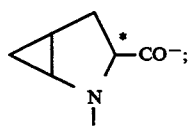
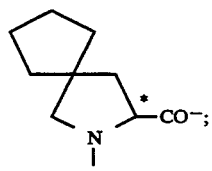
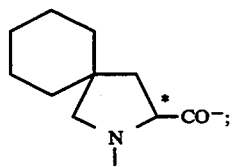
-continued
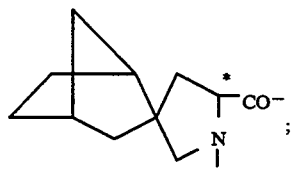
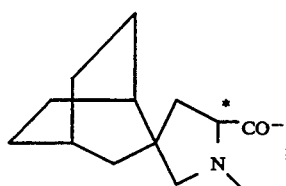
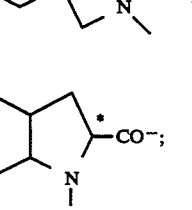
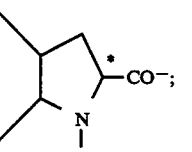
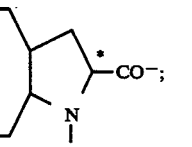
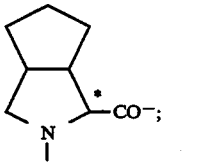
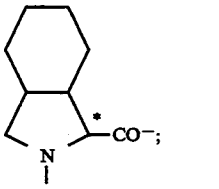
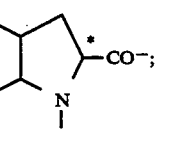
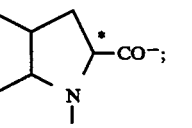

-continued

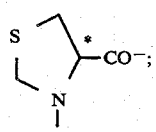

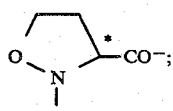

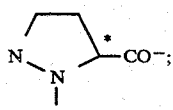

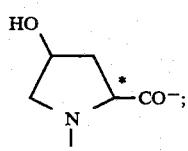

The heterocycles on which the abovementioned radicals are based are known, for example, from U.S. Pat. Nos. 4,344,949; 4,374,847; 4,350,704; EP-A 29,488; EP-A 31,741; EP-A 46,953; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids and also azaamino acids as components. The natural or unnatural amino acids, imino acids, azaamino acids and dipeptides can furthermore also be present as esters or amides, such as, for example, methyl ester, ethyl amide, semicarbazide or ω-amino-($C_4$–$C_8$)-alkyl amide.

Functional groups of the amino acids, imino acids and dipeptides can be present in protected form. Suitable protective groups such as, for example, urethane protective groups, carboxyl protective groups and side chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Physiologically tolerable salts of the compounds of the general formula I are in particular pharmaceutically utilisable or non-toxic salts.

Such salts are formed, for example, from compounds of the general formula I which contain acidic groups, for example carboxyl, with alkali metals alkaline earth metals, such as, for example, Na, K, Mg and Ca, and also with physiologically tolerable organic amines, such as, for example, triethylamine and tris(2-hydroxyethyl)amine.

Compounds of the general formula I which contain basic groups, for example an amino group or a guanidino group, form salts with organic acids, such as, for example, hydrochloric acid, sulphuric acid or phosphoric acid and with organic carboxylic or sulphonic acids, such as, for example, acetic acid, citric acid, benzoic acid, maleic acid, fumaric acid, tartaric acid and p-toluenesulphonic acid.

Preferred compounds of the general formula I are those in which

Y denotes —($CH_2$)$_m$—CO—, where m represents 1 or 2, or

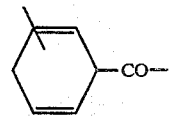

r denotes 1;
z denotes oxygen or sulphur;
W denotes hydroxyl, ($C_1$–$C_6$)-alkoxy, particularly methoxy, ethoxy or 2-propoxy;
r denotes hydrogen;
$R^1$ denotes —NH—C(=NH)—$NH_2$; —C(=NH)—$NH_2$ or —$CH_2$—$NH_2$ or methoxycarbonyl derivatives thereof;
$R^2$ denotes hydrogen or methyl;
$R^3$ denotes hydrogen; and
$R^4$ denotes —CO—NH—$R^5$, where —NH—$R^5$ represents an α-amino acid residue or the ω-amino-($C_2$–$C_8$)-alkyl amide thereof.

α-amino acid radicals representing —NH—$R^5$ here are particularly preferably the valine, lysine, phenylalanine or phenylglycine residues. A particularly preferred ω-($C_2$–$C_8$)-alkyl amide is the 4-aminobutyl amide.

The compounds of the general formula I according to the invention can be prepared by fragment condensation of a compound of the general formula III

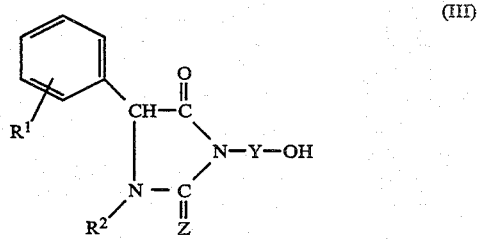

with a compound of the general formula IV

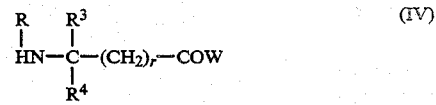

where r and the radicals R, $R^1$ to $R^4$ and Y, Z and W are defined as indicated above.

The starting peptides of the formula IV are synthesised, as a rule, stepwise from the C-terminal end. For condensation of the compounds of the general formula III with those of the general formula IV, the coupling methods of peptide chemistry known per se are advantageously used (see, for example, Houben-Weyl, Methoden der organischen Chemie (Methods of organic chemistry), Volume 15/1 and 15/2, Stuttgart, 1974). To do this, it is necessary as a rule that amino groups contained in $R^1$ and $R^4$ are protected during the condensation by reversible protective groups. The same applies to the carboxyl groups of the compound of the general formula IV, which are preferably present as ($C_1$-$C_6$)-alkyl, benzyl or tert-butyl esters. Protection of amino groups is unnecessary if the amino groups to be generated are still present as nitro or cyano groups and are only formed after coupling by hydrogenation. After coupling, the protective groups present are removed in a suitable manner. For example, $NO_2$ groups (guanidino protection), benzyloxycarbonyl groups and benzyl esters can be removed by hydrogenation. Protective groups of the tert-butyl type are cleaved by acid, while the 9-flourenylmethoxycarbonyl radical is removed by secondary amines.

The starting compounds of the general formula III can be obtained as follows:

By reaction of amino acids, N-alkylamino acids or preferably their esters (for example methyl, ethyl, benzyl or tert-butyl esters) (for example of a compound of the general formula V

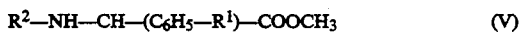

$$R^2-NH-CH-(C_6H_5-R^1)-COOCH_3 \quad (V)$$

with an isocyanatoalkanecarboxylic acid ester, an isothiocyanatoalkanecarboxylic ester, or an isocyanate or isothiocyanate of the aminobenzoic acid, for example of the general formula VI

$$Z=C=N-Y-COOCH_3 \quad (VI)$$

in which $R^1$, $R^2$, Y and Z are defined as indicated above, urea or thiourea derivatives are obtained, for example of the general formula VII

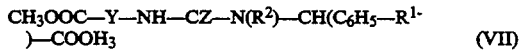

$$CH_3OOC-Y-NH-CZ-N(R^2)-CH(C_6H_5-R^{1-})-COOH_3 \quad (VII)$$

which cyclise by heating with acid with hydrolysis of the ester functions to give compounds of the general formula III. During the cyclisation, guanidino groups can be blocked by protective groups, (for example $NO_2$ or Mtr). Amino groups in the side chain can likewise be present in protected form (for example as Boc or Z derivatives) or still as an $NO_2$ or cyano function which can later be reduced to the amino group or, in the case of the cyano group, also converted into the formamidino group.

Otherwise, hydantoins of the general formula VIII

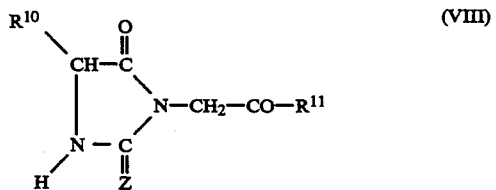

(VIII)

in which $R^{10}$ denotes any desired amino acid side chain and $R^{11}$ denotes an amide, an amino acid residue or a peptide residue, very commonly result by basic treatment of alkoxycarbonyl peptides or aralkoxycarbonyl peptides of the general formula IX

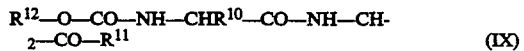

$$R^{12}-O-CO-NH-CHR^{10}-CO-NH-CH_2-CO-R^{11} \quad (IX)$$

in which $R^{10}$ and $R^{11}$ are defined as indicated above and $R^{12}$ denotes benzyl or tert-butyl (J. S. Fruton and M. Bergmann, J. Biol. Chem. 145 (1942) 253–265; C. A. Dekker, S. P. Taylor, jr. and J. S. Fruton, J. Biol. Chem. 180 (1949) 155–173; M. E. Cox, H. G. Carg, J. Hollowood, J. M. Hugo, P. M. Scopes and G. T. Young, J. Chem. Soc. (1965) 6806–6813; W. Voelter and A. Altenburg, Liebigs Ann. Chem. (1983) 1641–1655; B. Schwenzer, E. Weber and G. Losse, J. Prakt. Chem. 327 (1985) 479–486). In this case, however, the N-terminal amino acid racemises and the hydantoin hydrolyses to the urea derivative

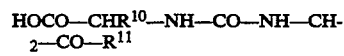

$$HOCO-CHR^{10}-NH-CO-NH-CH_2-CO-R^{11}$$

(W. Voelter and A. Altenburg, Liebigs Ann. Chem. (1983) 1641–1655).

In comparison, a mild method is cyclisation to give the hydantoins of compounds of the general formula X by treatment with tetrabutylammonium fluoride in tetrahydrofuran under reflux (J. Pless, J. Org. Chem. 39 (1974) 2644–2646).

A further possibility of a mild cyclisation is trimethylsilylation of the peptide bond between the N-terminal amino acid and the following glycine using bistrimethylsilyltrifluoroacetamide in acetonitrile (4 hours under reflux) (J. S. Davies, R. K. Merritt and R. C. Treadgold, J. Chem. Soc. Perkin Trans. I (1982) 2939–2947).

The guanylation of the amino function can be carried out using the following reagents:
1. O-Methylisothiourea (S. Weiss and H. Krommer, Chemiker Zeitung 98 (1974) 617–618),
2. S-Methylisothiourea (R. F. Borne, M. L. Forrester and I. W. Waters, J. Med. Chem. 20 (1977) 771–776),
3. Nitro-S-methylisothiourea (L. S. Hafner and R. E. Evans, J. Org. Chem. 24 (1959) 1157),
4. Formamidinosulphonic acid (K. Kim, Y.-T. Lin and H. S. Mosher, Tetrah. Lett. 29 (1988) 3183–3186),
5. 3,5-Dimethyl-1-pyrazolylformamidinium nitrate (F. L. Scott, D. G. O'Donovan and J. Reilly, J. Amer. Chem. Soc. 75 (1953) 4053–4054).
6. N,N'-di-tert-Butoxycarbonyl-S-methylisothiourea (R. J. Bergeron and J. S. McManis, J. Org. Chem. 52 (1987), 1700–1703).

Formamidines can be prepared from the corresponding cyano compounds by addition of alcohols (for example methanol or ethanol) in acidic anhydrous medium (for example dioxane, methanol or ethanol) and subsequent treatment with ammonia in alcohols (for example isopropanol, methanol or ethanol) (G. Wagner, P. Richter and Ch. Garbe, Pharmazie 29 (1974) 12–55).

A further method of preparing formamidines is the addition of $H_2S$ to the cyano group, followed by methylation of the resulting thioamide and subsequent reaction with ammonia (GDR Patent No. 235,866).

A further method for the preparation of the compounds of the general formula III is the reaction of compounds of the formula X

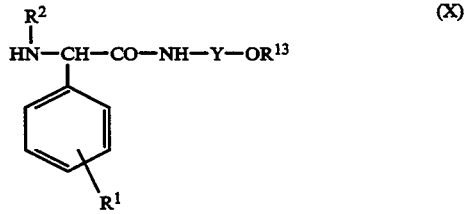

(X)

where $R^{13}$ denotes hydrogen or ($C_1$-$C_6$)-alkyl, with phosgene, thiophosgene or appropriate equivalents to give the esters of the imidazolidine derivatives, which can then be hydrolysed to the carboxylic acids (analogously to S. Goldschmidt and M. Wick, Liebigs Ann. Chem. 575 (1952) 217–231, C. Tropp. Chem. Ber. 61, (1928) 1431–1439).

The compounds of the general formula I and their physiologically tolerable salts can be administered as medicines per se, in mixtures with one another or in the form of pharmaceutical preparations which permit enteral or parenteral use and which contain, as active constituent, an effective dose of at least one compound of the general formula I or of a salt thereof, in addition to customary pharmaceutically innocuous excipients and additives. The preparations normally contain about 0.5 to 90% by weight of the therapeutically active compound.

The medicines can be administered orally, for example in the form of pills, tablets, coated tablets, sugar-coated tablets, granules, hard and soft gelatine capsules, solutions, syrups, emulsions or suspensions, or aerosol mixtures. Administration can also be carried out, however, rectally, for example in the form of suppositories, or parenterally, for example in the form of injection solutions, microcapsules or rods, percutaneously, for example in the form of ointments or tinctures, or nasally, for example in the form of nasal sprays.

The pharmaceutical preparations can be prepared in a manner known per se, pharmaceutically inert inorganic or organic excipients being used. For the preparation of pills, tablets, sugar-coated tablets and hard gelatine capsules, lactose, maize starch or derivatives thereof, talc, stearic acid or its salts, etc., for example, can be used. Excipients for soft gelatine capsules and suppositories are, for example, fats, waxes, semi-solid and liquid polyols, natural or hardened oils, etc. Suitable excipients for the preparation of solutions and syrups are, for example, water, sucrose, invert sugar, glucose, polyols etc. Suitable excipients for the preparation of injection solutions are water, alcohols, glycerol, polyols or vegetable oils, etc. Suitable excipients for microcapsules, implants or rods are, for example, copolymers of glycolic acid and lactic acid.

Apart from the active compounds and excipients, the pharmaceutical preparations can additionally contain additives such as, for example, fillers, extenders, disintegrants, binders, lubricants, wetting agents, stabilisers, emulsifiers, preservatives, sweeteners, colorants, flavourings or aromatisers, thickeners, diluents, buffer substances, and also solvents or solubilisers or agents for achieving a depot effect as well as salts for changing the osmotic pressure, coating agents or antioxidants. They can also contain two or more compounds of the general formula I or their pharmacologically acceptable acid addition salts and additionally one or more other therapeutically active substances.

Other therapeutically active substances of this type are, for example, agents promoting the circulation, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanthanoglycosides; coronary dilators, such as carbocromen; dipyramidol, nifedipine and perhexiline; antianginal compounds, such as isosorbide dinitrate, isosorbide mononitrate, glycerol nitrate, molsidomine and verapamil; β-blockers, such as propranolol, oxprenolol, atenolol, metoprolol and penbutolol. The compounds may moreover be combined with other nootropic substances, such as, for example, piracetam, or CNS-active substances, such as pirlindol, sulpiride, etc.

The dose can vary within wide limits and is to be adapted to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration the daily dose is in general about 0.01 to 0.3 mg/kg, preferably 0.05 to 0.1 mg/kg, of body weight. The daily dose is normally divided, in particular in the case of the administration of relatively large amounts, into several, for example 2, 3 or 4, part administrations. In some cases, depending on individual behaviour, it may be necessary to deviate upwards or downwards from the given daily dose. Pharmaceutical preparations normally contain 0.2 to 50 mg, preferably 0.5 to 10 mg, of active compound of the general formula I or one of its physiologically tolerable salts per dose.

The compounds of the formula I according to the invention have the ability to inhibit cell-cell adhesion which is due to the interaction of Arg-Gly-Asp-containing proteins, such as fibronectin, fibrinogen or the von Willebrand factor, with the so-called integrins. Integrins are transmembrane glycoproteins, receptors for Arg-Gly-Asp-containing cell matrix glycoproteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). They additionally inhibit the binding of other adhesive proteins, such as vitronectin, collagen and laminin, to the corresponding receptors on the surface of various types of cell.

The compounds of the general formula I according to the invention inhibit platelet aggregation, the metastasis of carcinoma cells and osteoclast binding to the bone surfaces.

The compounds of the formula I according to the invention are used acutely in risk of thrombosis and chronically in the prevention of arteriosclerosis and thrombosis, for example in the therapy and prophylaxis of arterial vascular diseases, such as in acute myocardial infarct, secondary prevention of myocardial infarct, reocclusion prophylaxis after lysis and dilatation (PCTA), unstable angina pectoris, transitory ischaemic attacks, strokes, coronary bypass operation including bypass reocclusion prophylaxis, pulmonary embolism, peripheral arterial occlusive disease, dissecting aneurysm; in the therapy of venous and microcirculatory vascular disorders, such as deep vein thrombosis, disseminated intravascular clotting, post-operative and post-partum trauma, surgical or infectious shock, septicaemia or in hyperactive platelet diseases, thrombotic thrombocytopenic purpura, preeclampsia, premenstrual syndrome, dialysis or extra-corporeal circulation; a further use is during cancer operations and also prophylactically in cancer. Osteoporosis can also be prevented by inhibition of osteoclast binding to the bone surface.

The compounds are tested in particular for their inhibitory action in blood platelet aggregation and the adhesion of fibrinogen to blood platelets. Gel-filtered blood platelets from human donor blood are used, which are activated with ADP or thrombin.

The inhibition of the binding of fibrinogen to its receptor (glycoprotein IIb/IIIa) by the compounds according to the invention is tested on intact, gel-filtered human platelets. The $K_i$ value of the inhibition of binding of $^{125}$I-fibrinogen after stimulation with ADP (10

μM) is given. (References: J. S. Bennett and G. Vilaire, J. Clin. Invest. 64 (1979), 1393–1401; E. Kornecki et al., J. Biol. Chem. 256 (1981), 5695–5701; G. A. Marguerie et al., J. Biol. Chem. 254 (1979), 5357–5363; G. A. Marguerie et al., J. Biol. Chem. 255 (1980), 154–161).

In this test, the following results are obtained for the compounds of Examples 1 and 2 which follow:

| Example | Ki (μM), ADP-stimulated |
|---------|-------------------------|
| 1       | 0.03                    |
| 2       | 2                       |

As a functional test, the inhibition of aggregation of gel-filtered human platelets by the compounds according to the invention is measured after ADP or thrombin stimulation. The $IC_{50}$ value of the inhibition is given. (Reference: G. A. Marguerie et al., J. Biol. Chem. 254 (1979), 5357–5363)

In this test, the following results are obtained for the compounds of Examples 1 and 2 which follow:

| Example | ADP-stimulated $IC_{50}$ (μM) | Thrombin-stimulated $IC_{50}$ 9 (μM) |
|---------|-------------------------------|---------------------------------------|
| 1       | 0.2                           | 0.07                                  |
| 2       | 6                             | 3                                     |

EXAMPLES

The products were identified by means of mass spectra and/or NMR spectra.

Example 1

(5-(4-Guanidinophenyl)-2,4-dioxoimidazolin-3-yl)acetyl-L-aspartyl-L-phenylglycine 1a: N-(1-Methoxycarbonyl-(4-aminophenyl)methyl),N'-ethoxycarbonylmethylurea 870 mg (4 mmol) of 4-aminophenylglycine methyl ester dihydrochloride are dissolved in 10 ml of dimethylformamide. After addition of 1 ml (8 mmol) of N-ethylmorpholine, 520 mg (4 mmol) of methyl isothiocyanatoacetate are added dropwise at −20° C. The mixture is allowed to warm to room temperature and is stirred for 15 hours at room temperature and concentrated, the residue is dissolved in the ethyl acetate and the solution is extracted with a dilute potassium hydrogen sulphate solution. After drying, the organic solution is concentrated.

Yield: 1.2 g

1b: (5-(4-Aminophenyl)-2,4-dioxoimidazolidin-3-yl)acetic acid 1.2 g (3.9 mmol) of N-(1-methoxycarbonyl-(4-aminophenylmethyl), N-ethoxycarbonylmethylurea are heated under reflux for 30 minutes in 20 ml of 6N hydrochloric acid and the mixture is concentrated in vacuo.

Yield: 1.0 g (92%)

1c: (5-(4-Nitroguanidinophenyl)-2,4-dioxoimidazolidin-3-yl)acetic acid 680 mg (5 mmol) of nitro-S-methylisothiourea and 1 g (3.5 mmol) of (5-(4-aminophenyl)-2,4-dioxoimidazolidin-3-yl)acetic acid are stirred at 80° C. for 7 h in 37 ml of 0.1 molar sodium hydroxide solution. After cooling, the mixture is extracted with methylene chloride, and the aqueous phase is subjected to clarifying filtration and acidified to pH 3 with dilute hydrochloric acid. After concentration, the residue is chromatographed for purification on Sephadex LH20 using a homogeneous mixture of butanol/glacial acetic acid/water.

Yield: 460 mg

1d: (5-(4-Nitroguanidinophenyl)-2,4-dioxoimidazolidin-3-yl)-acetyl-L-aspartyl (OtBu)-L-phenylglycine-OtBu 55 mg (0.477 mmol) of N-ethylmorpholine and 108 mg (0.523 mmol) of DCC are added at 0° C. to a solution of 160 mg (0.475 mmol) of (5-4-nitroguanidinophenyl)-2,4-dioxoimidazolidin-3yl)acetic acid, 204 mg (0.475 mmol) of H-Asp(OtBu)phenylglycine-OtBu hydrochloride and 65 mg (0.48 mmol) of hydroxybenzotriazole in 10 ml of dimethylformamide. The mixture is stirred at 0° C. for 1 hour and subsequently at room temperature for 5 hours. The precipitated urea is filtered off with suction, the filtrate is concentrated and the crude product is chromatographed on a silica gel column using ethyl acetate/methanol=95:5.

Yield: 304 mg (92%)

1e: (5-(4-Guanidinophenyl)-2,4-dioxoimidazolidin-3-yl)acetyl-L-aspartyl-L-phenylglycine 300 mg (0.43 mmol) of (5-(4-nitroguanidinophenyl)-2,4-dioxoimidazolidin-3-yl)-acetyl-L-aspartyl-L-aspartyl(OtBu)-L-phenylglycine-OtBu are allowed to stand at room temperature for 3 hours in 10 ml of 95 per cent trifluoroacetic acid with occasional shaking and the mixture is concentrated. The residue is dissolved in 50 ml of methanol and, after addition of 50 mg of 10% Pd on carbon, hydrogenated at room temperature for 5 h. The catalyst is filtered off, the filtrate is concentrated and the residue is chromatographed for purification on Sephadex LH20 using a homogeneous mixture of butanol/glacial acetic acid/water.

Yield: 137 mg FAB-MS 540 (M+H)+

Example 2

(5-(3-Guanidinophenyl)-2,4-dioxoimidazolidin-3-yl)-acetyl-L-aspartyl-L-phenylglycine This compound was prepared analogously to the method described in Example 1, starting from (5-(3-aminophenyl)-2,4-dioxoimidazolidin-3-yl)acetic acid. FAB-MS 540 (M+H)+

Example 3

(5-(4-Formamidinophenyl)-2,4-dioxoimidazolidin-3-yl)-acetyl-L-aspartyl-L-phenylglycine

Example 4

(5-(4-Aminomethylphenyl)-2,4-dioxoimidazolidin-3-yl)-acetyl-L-aspartyl-L-phenylglycine

Example 5

(5-(4-Formamidinophenyl)-4-oxo-2-thioxoimidazolidin-3-yl)acetyl-L-aspartyl-L-phenylglycine

Example 6

(5-(4-Formamidinophenyl)-4-oxo-2-thioxoimidazolidin-3-yl)acetyl-L-aspartyl-L-lysine

Example 7

(5-(4-Formamidinophenyl)-4-oxo-2-thioxoimidazolidin-3-yl)acetyl-L-aspartyl-L-valine

Example 8

(5-(4-Guanidinophenyl)-4-oxo-2-thioxoimidazolidin-3-yl)-acetyl-L-aspartyl-L-phenylglycine

Example 9

(5-(4-Aminomethylphenyl)-2,4-dioxoimidazolidin-3-yl)-acetyl-L-aspartyl-L-phenylalanine (4-aminobutyl)amide

Example 10

(5-(4-Methoxycarbonylguanidinophenyl)-2,4-dioxoimidazolidin-3-yl)acetyl-L-aspartyl-(OMe)-L-phenylglycine methyl ester

Example 11

(5-(R)-(4-Aminomethylphenyl)-2,4-dioxoimidazolidin-3-yl)acetyl-L-aspartyl-L-phenylglycine a) 4-Benzyloxycarbonylaminomethyl-D-phenylglycine 1 g of 4-aminomethyl-D-phenylglycine is dissolved in 7 ml of water and treated with 1.1 g of $CuCO_3$.$Cu(OH)_2$.$0.5H_2O$. The mixture is boiled under reflux for 45 min, allowed to cool and rendered alkaline (above pH 9) using 2N sodium hydroxide solution, 0.13 ml of benzyloxycarbonyl chloride is added and 2N sodium hydroxide solution is allowed to drip in with stirring at 0° C. with pH checking. The pH should not fall below pH 9. If all of the benzyloxycarbonyl chloride has reacted (no pH change), the precipitate is filtered off with suction.

Yield: 1.74 g.

The precipitate is dissolved in about 40 ml of 1N HCl at about 55° C. $H_2S$ is passed in at 50°-60° C. until the solution has been decolourised. The CuS is filtered off and the solution is neutralised with 10 per cent $NH_3$ solution. A precipitate is deposited, which is filtered off with suction and washed successively with water, ethanol and ether.

Yield: 300 mg.

b) 4-Benzyloxycarbonylaminomethyl-D-phenylglycine methyl ester hydrochloride 300 mg of 4-benzyloxycarbonylaminomethyl-D-phenylglycine are suspended in 3 ml of methanol and treated at 0° C. with 97 µl of $SOCl_2$. The mixture is heated with stirring at 40° C. for 4 hours. It is then concentrated in vacuo and the residue is triturated with ether.

Yield: 292 mg.

c) N-(1-(R)-(4-Benzyloxycarbonylaminomethylphenyl)-1-methoxycarbonylmethyl),N'-ethoxycarbonylmethylurea 290 mg of 4-benzyloxycarbonylaminomethyl-D-phenylglycine methyl ester hydrochloride are dissolved in 1.5 ml of dimethylformamide. 99 µl of ethyl isocyanatoacetate and 122 µl of triethylamine are added successively to this mixture at 0° C. The pH is adjusted to 8 using a little triethylamine. The mixture is allowed to come to room temperature and the dimethylformamide is removed by distillation in vacuo the next day. The residue is partitioned between ethyl acetate and water, and the ethyl acetate phase is separated off and extracted with $KHSO_4/K_2SO_4$ buffer, saturated $NaHCO_3$ solution and water, dried over $Na_2SO_4$ and concentrated.

Yield: 310 mg.

d) (5-(R)-(4-Aminomethylphenyl)-2,4-dioxoimidazolidin-3-yl)-acetic acid hydrochloride 280 mg of N-(1-(R)-(4-benzyloxycarbonylaminomethylphenyl-1-methoxycarbonylmethyl),N'-ethoxycarbonylmethylurea are boiled under reflux for 45 min in 4 ml of 6N HCl and the mixture is then concentrated and dried over KOH.

Yield: 180 mg.

e) (5-(R)-(4-tert-Butoxycarbonylaminomethylphenyl)-2,4-dioxoimidazolidin-3-yl)acetic acid A solution of 180 mg (0.6 mmol) of (5-(R)-(4-aminomethylphenyl)-2,4-dioxoimidazolidin-3-yl)acetic acid hydrochloride in a mixture of 2 ml of dioxane and 1 ml of water is adjusted to pH 8-9 at 0° C. using about 1 ml of 1N NaOH. 142 mg of di-tert-butyl dicarbonate are added to this mixture and it is stirred at room temperature for 3 hours. The mixture is then concentrated in a rotary evaporator and the residue is partitioned between ethyl acetate and water which has been acidified to pH 2 with $KHSO_4$. The ethyl acetate phase is then extracted twice by shaking with saturated $NaHCO_3$ solution. The combined $NaHCO_3$ solutions are acidified to pH 2 using $KHSO_4$ and extracted three times with ethyl acetate. The combined ethyl acetate phases are washed with water, dried over $Na_2SO_4$ and concentrated.

Yield: 180 mg.

f) (5-(R)-(4-tert-Butoxycarbonylaminomethylphenyl)-2,4-dioxoimidazolidin-3-yl)acetyl-L-aspartyl-L-phenylglycine di-tert-butyl ester 55.5 µl of N-ethylmorpholine and 97 mg of dicyclohexylcarbodiimide are added at 0° C. to a suspension of 160 mg (0.44 mmol) of (5-(R)-(4-tert-butoxycarbonylaminomethylphenyl)-2,4-dioxoimidazolidin-3-yl)acetic acid, 183 mg of H-Asp(OtBu)-Phg-OtBu hydrochloride and 60 mg of HOBt in 10 ml of dimethylformamide. The mixture is stirred at 0° C. for 1 hour and at room temperature for 3 hours. The precipitate is then filtered off with suction and the filtrate is concentrated. The residue is partitioned between ethyl acetate and water, and the ethyl acetate phase is separated off and extracted with $KHSO_4/K_2SO_4$ buffer, saturated $NaHCO_3$ solution and water, dried over $Na_2SO_4$ and concentrated.

Yield: 340 mg.

g) (5-(R)-(4-Aminomethylphenyl)-2,4-dioxoimidazolidin-3yl)-acetyl-L-aspartyl-L-phenylglycine 310 mg of (5-(R)-(4-tert-butoxycarbonylaminomethylphenyl)-2,4-dioxoimidazolidin-3-yl)acetyl-L-aspartyl-L-phenylglycine di-tert-butyl ester are dissolved in 3.1 ml of 90% strength aqueous trifluoroacetic acid. The mixture is allowed to stand at room temperature for 45 min and is concentrated, and the residue is partitioned between water and ether. The aqueous phase is freeze-dried.

Yield: 200 mg.

For purification, the substance is chromatographed in water on Sephadex LH20.

Yield: 180 mg. FAB-MS: 512.2 (M+H)+

Example 12

(5-(4-Guanidinophenyl)-2,4-dioxoimidazolidin-3-yl)acetyl-D-aspartyl-L-phenylglycine
FAB-MS: 540.2 (M+H)+

Example 13

(5-(4-Benzyloxycarbonylguanidinophenyl)-2,4-dioxoimidazolidin-3-yl)acetyl-L-aspartyl-L-phenylglycine diisopropyl ester 620 mg of dicyclohexylcarbodiimide are added at 0° C. to a suspension of 1.2 g (2.8 mmol) of 5-(4-benzyloxycarbonylguanidinophenyl)-2,4-dioxoimidazolidin-3-yl)acetic acid and 380 mg of HOBt in 180 ml of dimethylformamide and the mixture is stirred at 0° C. for 2 hours. 1.28 g (3.3 mmol) of H-Asp-Phg diisopropyl ester hydrochloride and 640 mg of N-ethylmorpholine are then added. The mixture is stirred at 0° C. for 1 hour and at room temperature for 3 hours. The precipitate is then filtered off with suction and the filtrate is concentrated. The residue is partitioned between ethyl acetate and water, and the ethyl acetate phase is separated off and extracted with $KHSO_4/K_2SO_4$ buffer, saturated $NaHCO_3$ solution and water, dried over $Na_2SO_4$ and concentrated.

Yield: 2.1 g. Melting point: $\approx 110°$ C. FAB-MS: 758.3 $(M+H)^+$

Example 14

(5-(4-Guanidinophenyl)-2,4-dioxoimidazolidin-3-yl)acetyl-L-aspartyl-L-phenylglycine diisopropyl ester hydrochloride 1.0 g (1.32 mmol) of 5-(4-benzyloxycarbonylguanidinophenyl)-2,4-dioxoimidazolidin-3-yl)acetyl-L-aspartyl-L-phenylglycine diisopropyl ester are dissolved in 200 ml of methanol and hydrogenated at room temperature in the presence of 0.1 g of 10% Pd/C. The pH is maintained at 4 during this reaction by dropwise addition of methanolic hydrochloric acid. After the end of the hydrogenation, the catalyst is filtered off and the filtrate is concentrated.

Yield: 850 mg FAB-MS: 624.2 $(M+H)^+$

The following compounds can be prepared analogously to these Examples:

Example 15

(5-(4-Guanidinophenyl)-2,4-dioxoimidazolidin-3-yl)acetyl-L-aspartyl-L-phenylglycine diethyl ester hydrochloride Melting point: $\approx 150°$ C. FAB-MS: 596.3 $(M+H)^+$

Example 16

(5-(4-Di(methoxycarbonyl)guanidinophenyl)-2,4-dioxoimidazolidin-3-yl)acetyl-L-aspartyl-L-phenylglycine diethyl ester Melting point: $\approx 100°$ C. FAB-MS: 712.3 $(M+H)^+$

Example 17

(5-(4-Benzyloxycarbonylguanidinophenyl)-2,4-dioxoimidazolidin-3-yl)acetyl-L-aspartyl-L-phenylglycine diisobutyl ester Melting point: $\approx 110°$ C. FAB-MS: 786.7 $(M+H)^+$

Example 18

(5-(4-Guanidinophenyl)-2,4-dioxoimidazolidin-3-yl)acetyl-L-aspartyl-L-phenylglycine diisobutyl ester acetate Melting point: $>200°$ C. (decomp.) FAB-MS: 652.3 $(M+H)^+$

Example 19

(5-(4-Benzyloxycarbonylguanidinophenyl)-2,4-dioxoimidazolidin-3-yl)acetyl-L-aspartyl-L-phenylglycine dimethyl ester

FAB-MS: 702.3 $(M+H)^+$

Example 20

(5-(4-Guanidinophenyl)-2,4-dioxoimidazolidin-3-yl)acetyl-L-aspartyl-L-phenylglycine dimethyl ester hydrochloride

FAB-MS: 568.2 $(M+H)^+$

Example 21

(5-(4-Benzyloxycarbonylguanidinophenyl)-2,4-dioxoimidazolidin-3-yl)acetyl-L-aspartyl-L-phenylglycine

FAB-MS: 674.3 $(M+H)^+$

Example 22

(5-(4-Benzyloxycarbonylguanidinophenyl)-2,4-dioxoimidazolidin-3-yl)acetyl-L-aspartyl-L-phenylglycine methyl ester Melting point: $\approx 165°$ C. FAB-MS:688.5 $(M+H)^+$

Example 23

(5-(4-Methoxycarbonylguanidinophenyl)-2,4-dioxoimidazolidin-3-yl)acetyl-L-aspartyl-L-phenylglycine

FAB-MS: 598.3 $(M+H)^+$

Example 24

(5-(4-Methoxycarbonylguanidinophenyl)-2,4-dioxoimidazolidin-3-yl)acetyl-L-aspartyl-L-phenylglycine dimethyl ester

FAB-MS: 626.2 $(M+H)^+$

Example 25

(5-(4-Methoxycarbonylguanidinophenyl)-2,4-dioxoimidazolidin-3-yl)acetyl-L-aspartyl(O-isopropyl)-L-phenylglycine 1-hexadecyl ester

FAB-MS: 865.3 $(M+H)^+$

Example 26

(5-(4-Acetylguanidinophenyl)-2,4-dioxoimidazolidin-3-yl)acetyl-L-aspartyl-L-phenylglycine diisopropyl ester

FAB-MS: 666.3 $(M+H)^+$

Example 27

(5-(4-Aminomethylphenyl)-2,4-dioxoimidazolidin-3-yl)acetyl-L-aspartyl-L-phenylglycine diisopropyl ester hydrochloride

FAB-MS: 596.2 $(M+H)^+$

Example 28

(5-(4-Acetylaminomethylphenyl)-2,4-dioxoimidazolidin-3-yl)acetyl-L-aspartyl-L-phenylglycine diisopropyl ester

FAB-MS: 638.2 $(M+H)^+$

Example 29

(5-(4-Methoxycarbonylaminomethylphenyl)-2,4-dioxoimidazolidin-3-yl)acetyl-L-aspartyl-L-phenylglycine diisopropyl ester

FAB-MS: 654.2 $(M+H)^+$

Example 30

(5-(4-Aminomethylphenyl)-2,4-dioxoimidazolidin-3-yl)acetyl-L-aspartyl(O-isopropyl)-L-phenylglycine 2-(2-(2-hydroxyethoxy)ethoxy)ethyl ester hydrochloride

FAB-MS: 730.3 $(M+H)^+$

Examples A–H which follow relate to pharmaceutical preparations.

Example A

Emulsions containing 3 mg of active compound per 5 ml can be prepared according to the following recipe:

| | |
|---|---|
| Active compound | 0.06 g |
| Neutral oil | q.s. |
| sodium carboxymethylcellulose | 0.6 g |
| Polyoxyethylene stearate | q.s. |
| Pure glycerol | 0.6 to 2 g |
| Flavourings | q.s. |
| Water (demineralised or distilled) | to 100 ml |

Example B

Tablets can be prepared according to the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example C

The following composition is suitable for the preparation of soft gelatine capsules containing 5 mg of active compound per capsule:

| | |
|---|---|
| Active compound | 5 mg |
| Mixture of triglycerides from coconut oil | 150 mg |
| Capsule contents | 155 mg |

Example D

The following formulation is suitable for the preparation of sugar-coated tablets:

| | |
|---|---|
| Active compound | 3 mg |
| Maize starch | 100 mg |
| Lactose | 55 mg |
| Sec. calcium phosphate | 30 mg |
| Soluble starch | 3 mg |
| Magnesium stearate | 5 mg |
| Colloidal silica | 4 mg |
| | 200 mg |

Example E

Sugar-coated tablets containing an active compound according to the invention and another therapeutically active substance:

| | |
|---|---|
| Active compound | 6 mg |
| Propanolol | 40 mg |
| Lactose | 90 mg |
| Maize starch | 90 mg |
| Sec. calcium phosphate | 34 mg |
| Soluble starch | 3 mg |
| Magnesium stearate | 3 mg |
| Colloidal silica | 4 mg |
| | 270 mg |

Example F

Sugar-coated tablets containing an active compound according to the invention and another therapeutically active substance:

| | |
|---|---|
| Active compound | 5 mg |
| Pirlindol | 5 mg |
| Lactose | 60 mg |
| Maize starch | 90 mg |
| Sec. calcium phosphate | 30 mg |
| Soluble starch | 3 mg |
| Magnesium stearate | 3 mg |
| Colloidal silica | 4 mg |
| | 200 mg |

Example G

Capsules containing an active compound according to the invention and another therapeutically active substance:

| | |
|---|---|
| Active compound | 5 mg |
| Nicergoline | 5 mg |
| Maize starch | 185 mg |
| | 195 mg |

Example H

Injection solutions containing 1 mg of active compound per ml can be prepared according to the following recipe:

| | |
|---|---|
| Active compound | 1.0 mg |
| Polyethylene glycol 400 | 0.3 mg |
| Sodium chloride | 2.7 mg |
| Water for injection purposes to | 1 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Phenylimidazolidine derivatives of the general formula I $$R^1-\text{Ar}-CH-C(=O)-N-Y-N(R)-C(R^3)(R^4)-(CH_2)_r-COW \quad (I)$$

(with imidazolidine ring: N(R^2)—C(=Z))

in which

Y denotes $-(CH_2)_m-CO-$, where m represents an integer from 1 to 4, or (a phenylene-CO group)

r denotes a number from 0 to 3;

Z denotes oxygen or sulphur;

W denotes hydroxyl, $(C_1-C_{28})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$(C_1-C_{18})$-alkylamino;

$R^1$ denotes $-(CH_2)_n-NH-X$ or $-(CH_2)_p-C(=NH)-NH-X^1$, where n and p represent a number 0 to 3;

X, $X^1$ denote hydrogen, $(C_1-C_6)$-alkyl, $(C_1-C_6)$-alkoxycarbonyl, $(C_1-C_6)$-alkylcarbonyl, $(C_1-C_{18})$-alkylcarbonyl-oxy-$(C_1-C_6)$-alkoxycarbonyl, $(C_6-C_{14})$-aryloxycarbonyl, which can also be substituted in the aryl radical, $(C_6-C_{14})$-aryl$(C_1-C_6)$-alkoxycarbonyl which can also be substituted in the aryl radical, cyano, hydroxyl, $(C_1-C_6)$-alkoxy or amino, and X additionally denotes a radical of the formula II $$R'-NH-C(=N-R'') \qquad (II)$$

where
- R', R" independently of one another denote hydrogen, $(C_1-C_6)$-alkyl, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryloxycarbonyl, which can also be substituted in the aryl radical, $(C_6-C_{14})$-aryl$(C_1-C_6)$-alkoxycarbonyl which can also be substituted in the aryl radical, cyano, hydroxyl, $(C_1-C_6)$-alkoxy or amino; alkoxycarbonyl which can also be substituted in the aryl radical, cyano, hydroxyl, $(C_1-C_6)$-alkoxy or amino
- R, $R^2$ denote hydrogen or $(C_1-C_6)$-alkyl;
- $R^3$ denotes hydrogen, phenyl or substituted phenyl;
- $R^4$ denotes hydrogen, $-COOR^5$, $CO-N(CH_3)R^5$ or $-CO-NH-R^5$;
- $R^5$ denotes hydrogen or $(C_1-C_{28})$-alkyl which is optionally mono- or polysubstituted by identical or different radicals from the series consisting of hydroxyl, hydroxycarbonyl, aminocarbonyl, mono or di-$(C_1-C_{18})$-alkylaminocarbonyl, amino-$(C_2-C_{14})$-alkylaminocarbonyl, amino$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{14})$-alkylaminocarbonyl, phenyl-$(C_1-C_8)$-alkoxycarbonyl, which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, halogen, nitro, trifluoromethyl or a radical $R^6$, where
- $R^6$ denotes optionally substituted $(C_6-C_{14})$-aryl, optionally substituted $(C_6-C_{14})$-aryl-$(C_1-C_8)$-alkyl or a monocyclic or bicyclic 5- to 12-membered heterocyclic ring which can be aromatic, partially hydrogenated or completely hydrogenated and which, as the heteroelement, can contain one, two or three identical or different nitrogen, oxygen or sulphur atoms, or denotes a radical $R^7$, where the aryl radical and, independently thereof, the heterocyclic radical can be optionally monosubstituted or polysubstituted by identical or different radicals from the series consisting of $(C_1-C_{18})$-alkyl, $(C_1-C_{18})$-alkoxy, halogen, nitro, amino and trifluoromethyl;
- $R^7$ denotes $-NR^8R^9$, $-OR^8$, $-SR^8$, an amino acid side chain, a natural or unnatural amino acid residue, imino acid residue, optionally N-$(C_1-C_8)$-alkylated or $(C_6-C_{14})$-aryl-$(C_1-C_8)$-alkylated azaamino acid residue or dipeptide residue, which can also be substituted in the aryl radical and/or in which the peptide bond can be reduced to NH-CH$_2$, and also their esters and amides, where free functional groups can optionally be substituted by hydrogen or hydroxymethyl or protected by protective groups customary in peptide chemistry, or denotes a radical $-COR^{7'}$, in which $R^{7'}$ is defined as $R^7$;
- $R^8$ denotes hydrogen, $(C_2-C_{18})$-alkyl, optionally substituted $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkoxycarbonyl, where the alkyl groups can optionally be substituted by an amino group and/or where the aryl radicals can be monosubstituted or polysubstituted, preferably monosubstituted by identical or different radicals from the series consisting of $(C_1-C_8)$-alkyl, $(C_1-C_8)$-alkoxy, halogen, nitro, amino or trifluoromethyl, a natural or unnatural amino acid residue, imino acid residue, optionally N-$(C_1-C_8)$-alkylated or $(C_6-C_{14})$-aryl-$(C_1-C_8)$-alkylated azaamino acid residue or a dipeptide residue, which can also be substituted in the aryl radical and/or in which the peptide bond can be reduced to NH-CH$_2$; and
- $R^9$ denotes hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

and their physiologically tolerable salts.

2. Phenylimidazolidine derivatives according to claim 1, characterised in that

Y denotes $-(CH_2)_m-CO-$, where m represents 1 or 2, or

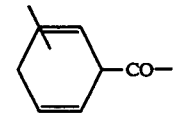

r denotes 1;
z denotes oxygen or sulphur;
W denotes hydroxyl, $(C_1-C_6)$-alkoxy, particularly methoxy, ethoxy or 2-propoxy;
R denotes hydrogen;
$R^1$ denotes $-NH-C(=NH)-NH_2$; $-C(=NH)-NH_2$ or $-CH_2-NH_2$ or methoxycarbonyl derivatives thereof;
$R^2$ denotes hydrogen or methyl;
$R^3$ denotes hydrogen; and
$R^4$ denotes $-CO-NH-R^5$, where $-NH-R^5$ represents an α-amino acid residue or the ω-amino-$(C_2-C_8)$-alkyl amide thereof.

3. Phenylimidazolidine derivatives according to claim 1, characterised in that
$R^4$ denotes $-CO-NH-R^5$, where $-NH-R^5$ represents the valine, lysine, phenylalanine or phenylglycine residue.

4. Phenylimidazolidine derivatives according to claim 1, characterised in that $R^4$ denotes $-CO-NH-R^5$, where $R^5$ represents the 4-aminobutyl amide of an α-amino acid.

5. Process for inhibiting platelet aggregation and thromboses, comprising administering to a patient in need thereof an effective dose of a compound according to claim 1.

6. Pharmaceutical preparation, characterised in that it contains one or more compounds of the general formula I of claim 1 or a physiologically tolerable salt thereof as active compound together with pharmaceutically acceptable excipients and additives and, optionally, also one or more other pharmacological active compounds.

* * * * *

UNITED STATES PATENT AND TRADEMARK OFFICE
CERTIFICATE OF CORRECTION

PATENT NO. : 5,424,293
DATED : June 13, 1995
INVENTOR(S) : Zoller et al

It is certified that error appears in the above-indentified patent and that said Letters Patent is hereby corrected as shown below:

Title page: under [*] Notice, should read -- The term of this patent shall not extend beyond the expiration date of Patent No: 5,389,614 --.
col. 2, line 13, delete comma "," after --($C_1$-$C_{18}$)--;
col. 8, line 10 and col. 22, line 30, replace " 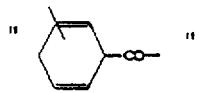 " with -- 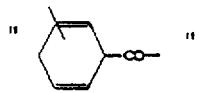 --;

col. 8, line 20, replace "r" with --R--;
col. 8, line 29, replace " -amino" with -- -Amino--;
col. 9, line 33, replace ")-$COOH_3$" with --)-$COOCH_3$--;
col. 13, line 25, replace "$IC_{50}$ 9µm)" with --$IC_{50}$(µm)--;
col. 14, line 23, delete "L-aspartyl-";
col. 16, line 41, replace "3 yl" with --3-yl--;
col. 20, line 50, correct "-CO" to read -- -CO- --;
col. 21, line 17, delete "alkoxy-" and delete lines 18 and 19.

Signed and Sealed this

Sixteenth Day of January, 1996

*Attest:*

BRUCE LEHMAN

*Attesting Officer*  Commissioner of Patents and Trademarks